United States Patent [19]

Kojima et al.

[11] Patent Number: 4,713,166
[45] Date of Patent: Dec. 15, 1987

[54] PUMP CELL ELEMENT FOR AIR-FUEL RATIO SENSOR

[75] Inventors: Takao Kojima; Hiroyuki Ishiguro, both of Nagoya, Japan

[73] Assignee: NGK Spark Plug Co., Ltd., Aichi, Japan

[21] Appl. No.: 875,077

[22] Filed: Jun. 17, 1986

[30] Foreign Application Priority Data

Jun. 18, 1985 [JP] Japan .................. 60-130703

[51] Int. Cl.$^4$ ............................. G01N 27/58
[52] U.S. Cl. .................... 204/425; 204/410; 204/429
[58] Field of Search .............. 204/410, 412, 425, 426, 204/429, 1 S

[56] References Cited

U.S. PATENT DOCUMENTS

| 4,101,403 | 7/1978 | Kita et al. | 204/410 |
| 4,304,652 | 12/1981 | Chiba et al. | 204/425 |
| 4,496,455 | 1/1985 | Linder et al. | 204/412 |
| 4,498,968 | 2/1985 | Yamada et al. | 204/412 |
| 4,510,036 | 4/1985 | Takeuchi et al. | 204/425 |

Primary Examiner—G. L. Kaplan
Attorney, Agent, or Firm—Wegner & Bretschneider

[57] ABSTRACT

A pump cell element, for an air-fuel ratio sensor, comprising an oxygen ion conductive zirconia solid electrolyte, a pair of layer electrodes coated on the both surface areas of a measuring portion, and ceramic coating layers each coated on each of said electrodes, at least one of said coating layers disposed on the electrode of a minus side of the pump cell element being provided uniformly and dispersedly with through-pores having a converted diameter of 20–500 μm with an average opening percentage of said through-pores is 5–20%. Blackening at the cathode is effectively eliminated.

15 Claims, 7 Drawing Figures

PUMP CELL ELEMENT FOR AIR-FUEL RATIO SENSOR

BACKGROUND OF THE INVENTION

The present invention relates to a sensor comprising zirconia base oxygen ion conductive solid electrolyte cells for measuring oxygen concentration or A/F-ratio ("A/F-ratio" means "air/fuel-ratio") in an exhaust-gas atmosphere of a combustion equipment, typically an internal combustion engine. Particularly, it relates to the structure of the sensor of the system combining a pump cell of above kinds and a sensor cell, and more specifically, a pump cell element for the pump cell.

For the measurement of oxygen concentration in the exhaust gas, there are usually used oxygen sensors of the system combining a pump cell and a sensor cell, which are comprised of zirconia base oxygen ion conductive solid electrolyte cell. This system is divided into two kinds of types, a closed compartment type and a gap compartment type. The Japanese Patent Kokai Publication No. 56-130649 discloses a closed compartment type sensor which measures an oxygen concentration in exhaust gas containing excess oxygen at a theoretical air-fuel ratio (about 14.5; excess air rate $\lambda = 1$) or more. And a gap compartment type sensor is disclosed in U.S. Pat. No. 4,498,968.

In either type of the sensors, an electric current $I_P$ for the pump cell is automatically adjusted in a pump cell disposed in an electric current controlling and measuring circuit for the pump cell, so that the output of the sensor cell produced by passing a pump electric current $I_P$ in a direction of pumping up oxygen to the side of exhaust gas from a closed compartment (or a gap compartment) may always indicate a certain constant value no matter how the oxygen concentration in the exhaust gas may change. In this case, $I_P$ changes in proportion to the oxygen concentration, which can be used to measure the oxygen concentration.

The voltage produced between the two electrodes of the pump cell becomes large at $P_{O_2}=0$, that is, at an oxygen concentration nearly corresponding to $I_P=0$. When this voltage is too large, a solid electrolyte plate (oxide sintered body) is reduced on the cathode side, and inner resistance comes to be increased due to occurence of so-called blackening. Further, when a pump electric current as well as an electric voltage are large, the blackening easily occurs.

Japanese Patent Kokai Publication No. 59-208453 discloses that in a gap compartment type sensor, the A/F-ratio of the exhaust gas at the fuel rich side (at the side of $\lambda < 1$) is measured in the same system as in the case of $\lambda > 1$.

Japanese Patent Kokai Publication No. 59-208455 discloses a system which causes a pump electric current to flow in the reverse direction in a gap compartment sensor, that is, the system which causes an electric current to flow in the reverse direction of transferring oxygen from the exhaust gas side to the gap compartment side, in order to measure the A/F-ratio of the exhaust gas at the fuel rich side.

SUMMARY OF THE DISCLOSURE

The gap compartment type is of a larger electric current type, and has a better responsibility, but tends to produce the blackening, compared with the closed compartment type. In both types, the blackening is produced at the anode side of a pump cell, that is, at the boundary layer among an electrode at a closed compartment (or an intermitting compartment) side, a solid electrolyte and a gas. In Japanese Patent Kokai Publication No. 59-208453, the blackening is more easily produced than in the case of $\lambda > 1$, especially, the less A/F-ratio becomes, the easier the blackening occurs. In Japanese Patent Kokai Publication No. 59-208455, the exhaust gas side becomes a cathode, where the blackening comes to occur easily. It tends to occur especially when a protective or insulating layer of ceramic is coated on the electrode of the cathode side.

Thus, in the case of solid electrolyte elements for pumping action, a porous ceramic layer is often provided on the surface of electrode for the purpose of protection and insulation, and a limit electric current value is determined depending on the amount of oxygen which can be diffused and passed in a unit time through these porous layers. That is, above this limited electric current value, the $ZrO_2$ element is subjected to the reduction such as blackening, etc. due to the applied electric current, which necessitates some limitation to the electric voltage (or current) to be applied to the $ZrO_2$ element. Further, the use of a thin coating layer for the purpose of applying high electric current thereto brings easily the deterioration of electrode materials under using conditions. Accordingly, conventional A/F sensors have a drawback in that they tend to cause the blackening in the solid electrolyte on the cathode side of the pump cell.

It is a primary object of the present invention to provide an air-fuel ratio sensor which eliminates the blackening on a cathode side of a pump cell element having an electric insulating-protective coating layer.

According to the aspect of the present invention, there is provided a pump cell element for an air-fuel ratio sensor, the pump cell element comprising:

an oxygen-ion conductive zirconia-solid electrolyte, a pair of layer electrodes coated on the both surface areas of a measuring portion, and ceramic coating layers each coated on each of said electrodes, at least one of said coating layers disposed on the electrode of a minus side of the pump cell element being provided uniformly and dispersedly with through-pores having a converted diameter of at least 20 $\mu$m.

The term "converted diameter" means a minimum value of the diameters or widths of a pore.

For the prevention of blackening due to the presence of a porous ceramic layer on a cathode surface, it might be proposed to increase the porosity of the porous ceramic layer. In this case, however, a considerable thickness (about 100 $\mu$m) is required for maintaining the durability and strength as the coating layer, wherein a relatively long path is required until oxygen reaches the electrode through the coating layer. Under such condition, when an electric current is applied for pumping of oxygen, the $ZrO_2$ solid electrolyte is often reduced due to an insufficient supply of oxygen.

In order to apply a large quantity of electric current thereto, hence, the amount of oxygen migration through the cathode side coating layer should be extremely large. Further, for maintaining a stable performance for a long period of time under the using condition of electrode, the protective coating layer should have mechanical and chemical strength. The above-described problems can be solved by the use of a ceramic coating layer provided uniformly and dispersedly with through-pores having a converted diameter of 20 to below 500 μm, preferably 80–450 μm, more preferably 300–450 μm. The through-pores are preferably disposed at an average opening percentage of through-pores of 5–20%, more preferably 5–15% and most preferably 10–15%, wherein pores having a diameter of below 20 μm are omitted in calculating the opening percentage.

Effects of the present invention are as follows. A solid electrolyte element for pumping action often has a porous coating material on the surface of an electrode, wherein an electric current-value limit is determined depending on the amount of oxygen diffusionable in a unit time through a porous coating material. Beyond the current value limit, the $ZrO_2$ element is subjected to reduction such as blackening, etc. due to electric current applied. Therefore, the conventional sensor has a defect in that the voltage (or electric current) applied to $ZrO_2$-element should be limited to some extent.

The present invention has an advantage that it does not require such limitation to electric power to be applied.

DESCRIPTION OF THE PREFERRED EMBODIMENTS

Figure 1:
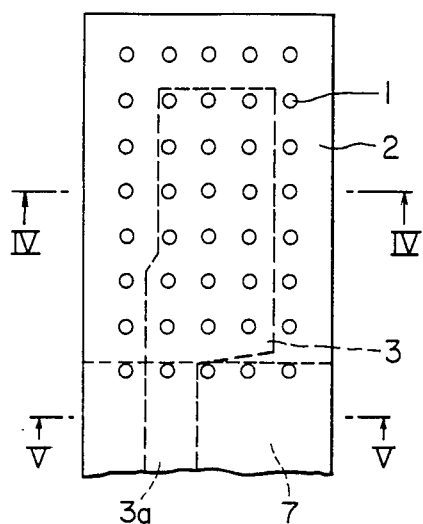
FIG. 1 is a schematic view showing the form and distribution of through-pores of a coating layer on an electrode-side surface in a pump cell element according to one embodiment of the present invention.
Figure 4:
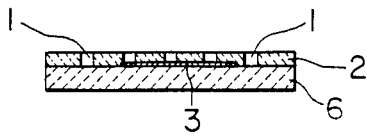
FIGS. 4 and 5 are cross sectional views taken along the lines IV—IV and V—V of FIG. 1, respectively.

The preferred embodiments will be described in detail. FIGS. 1 and 4 illustrate a schematic structure of a pump cell element for an air-fuel ratio sensor according to the present invention. Referring now to FIGS. 1 and 4, there is described a preferred embodiment.

The area other than through-pores 1 of a coated layer 2 can be either a dense layer, or a layer with pores of 1–10 μm diameter, wherein the dense layer (having no pores of 1 μm or larger) is preferred in view of the strength.

As described above, the converted diameter of the through-pores 1 of the coating layer on a cathode side is at least 20 μm. This is because the pore diameter becomes greater than the moving path diameter for molecules to bring a less diffusion resistance of oxygen. At a converted diameter of above 80 μm, the diffusion resistance is practically negligible. Meanwhile, in a converted diameter of 500 μm or more, the performance is deteriorated since the electrode in durable running is subjected to a toxic effect of lead in a gas to be measured.

As described above, an average opening percentage of the through-pores of at least 20 μm diameter is preferably 5–20%. This is because the electrode area is used efficiently so that a constant pump capacity (for example, $$\frac{200 \text{ mA}}{6.4 \text{ mm}^2} = 30 \text{ mA/mm}^2$$

or more) of a sensor is maintained. In an average opening percentage of the through-pores of above 20%, the coating layer can not obtain a sufficient strength. A coating layer 2 is $Al_2O_3$-base ceramics containing 60 wt % of $Al_2O_3$ for obtaining excellent insulating-property, high mechanical and chemical stabilities. It is more preferably $Al_2O_3$-base ceramics containing 80 wt % of $Al_2O_3$, most preferably $Al_2O_3$-base ceramics containing 90 wt % of $Al_2O_3$.

For obtaining a strong coating layer, the coating layer 2 is prepared by screen-printing etc. on a green or not-sintered zirconia solid electrolyte 6 and an electrode pattern 3, followed by sintering them simultaneously.

Through-pores 1 are provided either by preparing a previously (not-printed) mask part in screen-printing, etc. or by adding material to be vanished during sintering (for example saw dust, saccharose, etc.). The former is suitable for through-pores with relatively large diameters, while the latter is suitable for through-pores with relatively small diameters. Further, both the manners mentioned above can be used in combination.

Figure 2:
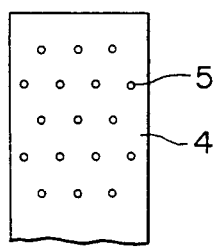
FIGS. 2 and 3 are schematic views showing the patterns of coating screens for providing through-pores.
Figure 3:
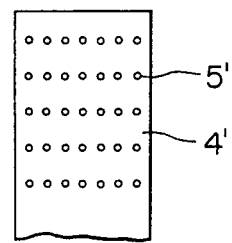

FIGS. 2 and 3 show the patterns of coating screens for providing a pump cell element for the air-fuel ratio sensor of the present invention, wherein there are provided screen-surfaces 4, 4' and the closed portions 5, 5' of screen (i.e., portions corresponding to through-pores).

Figure 5:
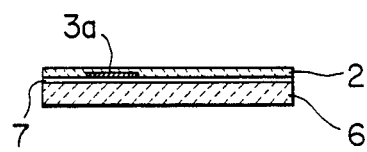
Figure 6:
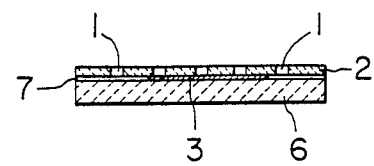
FIG. 6 is a cross sectional view of another embodiment taken along the line IV—IV of FIG. 1.

As shown in FIG. 5, a reinforcement coating layer 7 may be disposed on the supporting leg portion of the pump cell element between the zirconia solid electrolyte 6 and a lead pattern 3a (or additionally coating layer 2), while as shown in FIG. 6 the reinforcement coating layer 7 may be provided at the portion surrounding the electrode pattern 3. The reinforcement coating layer is preferably an insulating layer and may be dense alumina or the like ceramics. The layer arrangements as hereinabove mentioned can be applied on one side or both sides of the solid electrolyte (substrate) 6. An advantageous result will be achieved, when applied on both the sides, with respect to the strength and warp.

The present invention will be described in detail with reference to the following examples; however, the examples are not to be construed to limit the scope of the invention thereto.

EXAMPLES

Specimens shown schematically in FIG. 1 were prepared according to the following steps and tested with regard to applied current-durability.

1. 6 mol % of $Y_2O_3$ (purity: 99.99 wt %) were added to $ZrO_2$ (purity: 99.9 wt %), and mixed with each other for 10 hours to prepare an admixture.

2. After drying, the admixture was calcined at 1300° C. for 2 hours.

3. The calcined admixture was passed through 20-mesh screen, wet-pulverized for 50 hours, dried and passed again through a 20-mesh screen to obtain powder.

4. Methyl ethyl ketone (20 wt %) and toluene (15 wt %) were added to the obtained powder, and mixed with each other for 10 hours to obtain a slurry.

5. Resins such as BMS, DBP, etc. were added to the obtained slurry, and mixed with each other for 15 hours.

6. A sheet of a 0.8 mm thickness was prepared by means of a doctor-blade process.

7. A coating layer for reinforcement (50 μm thick) of dense alumina (92 wt % $Al_2O_3$, 3 wt % MgO, the balance being $SiO_2$, CaO, etc.) was coated on the leg portion of the obtained sheet where lead is disposed to prepare a coated sheet.

8. An electrode and a lead pattern were screen-printed in a thickness of 25 μm on the coated sheet by using a Pt-paste containing 10 wt % of base material (i.e., coating layer material).

9. (a) The coated sheet material of the step 7 was screen-printed in a thickness of 15 μm by means of coating-screens having pore patterns as shown in FIGS. 2 and 3 to obtain Specimens 1 and 3.

(b) The coated sheet material of the step 7 was screen-printed in a thickness of 15 μm by means of a screen having masked pore-portions appropriately for providing through-pores of 450 μm diameter to obtain Specimen 2.

(c) The coated sheet material of the step 7 was mixed with about 30 wt % of granular saccharose (grain size of 30 μm in Specimen 5, and grain size of 15 μm in Specimen 6), and screen-printed in a thickness of 15 μm by usual process.

(d) The coated sheet material of the step 7 was mixed with about 30 wt % of granular saccharose (grain size of 15 μm), and screen-printed in a thickness of 15 μm by means of a coating-screen to obtain Specimen 4.

(e) The coated sheet material of the step 7 was screen-printed in a thickness of 15 μm by usual process to obtain Specimen 7.

10. A lead-wire was provided by means of Pt-wire (diameter of 0.3 mm).

11. After removing binders at 250° C. for 10 hours, Specimens were sintered at 1515° C. for 4 hours to obtain Specimens in a size of 4 mm width and 8 mm length.

Figure 7:
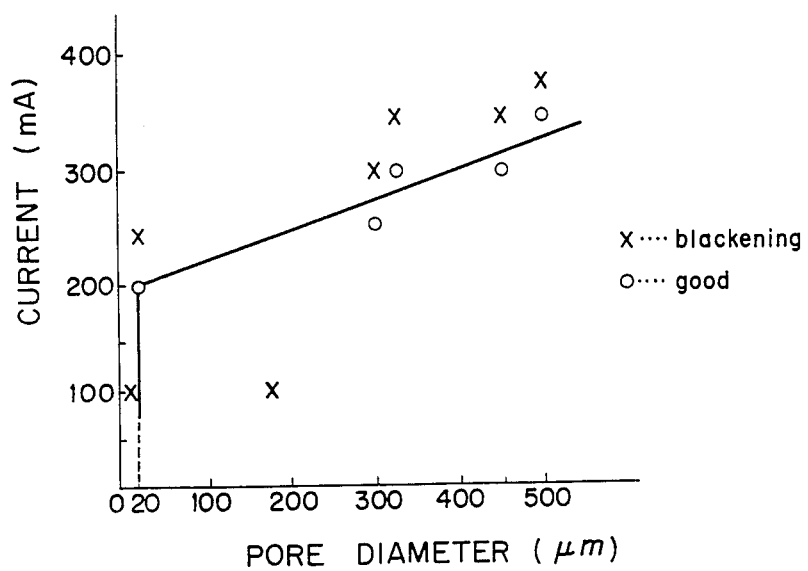
FIG. 7 is a graph showing the test results.

12. The Specimens were charged into an electric furnace at 1000° C., wherein electric currents of 100, 120, 150, 200, 250, 300, 350 and 400 mA were, in the recited order for 1 hour, respectively, by using DC-source, applied to each of the Specimens. The state of blackening was observed. The test results are shown in Table 1 and FIG. 7.

TABLE 1

| Specimen | Diameter of through-pore (μm) | Pore-opening percentage[1] (%) | Current applied (mA) | Remarks |
|---|---|---|---|---|
| X[2] | 1 | 500 | 10–15 | 400 | Pt deteriorated |
| | | | | 350 | good |
| A | 2 | 450 | 10–15 | 350 | deterioration |
| | | | | 300 | good |
| A | 3 | 300 | about 10 | 300 | blackening |
| | | | | 250 | good |
| A | 4 | 300 + 5 | 10–15 | 350 | blackening occurs |
| | | | | 300 | good |
| A | 5 | 20 | 5–10 | 250 | blackening |
| | | | | 200 | good |
| X | 6 | at most 10 | — | 100 | blackening[3] |
| X | 7 | porous | — | 100 | blackening |

[1]Opening percentage of through-pores having at least 20 μm diameter
[2]"A" is inventive Specimen, while "X" denotes "outside of the present invention".
[3]Specimen 6 was blackened at 30000 km in testing condition mounted on an engine.

It should be noted that modifications and applications apparent in the art may be made without departing from the gist of the present invention as disclosed and claimed.

We claim:

1. A pump cell element for an air-fuel ratio sensor, the pump cell element comprising:
an oxygen ion conductive zirconia solid electrolyte,
a pair of layer electrodes coated on the both surface areas of a measuring portion, and
ceramic coating layers each coated on each of said electrodes, at least one of said coating layers disposed on the electrode of a minus side of the pump cell element being provided uniformly and dispersedly with through-pores having a converted diameter of at least 20 but less than 500 μm.

2. The pump cell element according to claim 1, wherein said through-pores have an average opening percentage of 5–20%.

3. The pump cell element according to claim 2, wherein the average opening percentage of said through-pores is 5–15%.

4. The pump cell element according to claim 1, wherein both of said coating layers are provided with said through-pores.

5. The pump cell element according to claim 1, wherein said coating layer is applied on at least the entire surface area exposed to exhaust gas in said pump cell element, said coating layer being, except for said through-pores, a dense $Al_2O_3$-base sintered body having pores less than 1 μm to serve as a reinforcing layer of said pump cell element.

6. The pump cell element according to claim 1, wherein said through-pores have a converted diameter of 80–450 μm.

7. The pump cell element according to claim 6, wherein said through-pores have a converted diameter of 300–450 μm.

8. The pump cell element according to claim 1, wherein the average opening percentage of the through-pores is 10–15%.

9. The pump cell element according to claim 1, wherein said ceramic coating layers are $Al_2O_3$-base ceramics containing at least 60% by weight of $Al_2O_3$.

10. The pump cell element according to claim 9, wherein said ceramic coating layers are $Al_2O_3$-base ceramics containing at least 90% by weight of $Al_2O_3$.

11. The pump cell element according to claim 1, wherein said at least one of the ceramic coating layers has a thickness of at least about 100 μm.

12. A pump cell element for an air-fuel ratio sensor, the pump cell element comprising:
an oxygen ion conductive zirconia solid electrolyte,
a pair of layer electrodes coated on the surface areas of a measuring portion, and
ceramic coating layers each coated on each of said electrodes, at least one of said coating layers disposed on the electrode of a minus side of the pump cell element being provided uniformly and dispersedly with through-pores having a converted diameter of at least 20 but less than 500 μm, said ceramic coating layers having been produced by sintering with the zirconia solid electrolyte.

13. The pump cell element according to claim 12, wherein said through-pores have been formed by masking upon applying said ceramic coating layer.

14. The pump cell element according to claim 12, wherein said through-pores have been formed by incorporating material to be vanished during sintering.

15. The pump cell element according to claim 12, wherein said pump cell element further includes at least one reinforcement ceramic coating layer disposed on a supporting leg portion of the solid electrolyte.